United States Patent [19]

Wright et al.

[11] Patent Number: 5,091,412
[45] Date of Patent: Feb. 25, 1992

[54] ANTIVIRAL TERPENE HYDROQUINONES AND METHODS OF USE

[75] Inventors: Amy S. Wright, Fort Pierce, Fla.; Sue S. Cross, both of Fort Pierce, Fla.; Neal S. Burres, Highland Park, Ill.; Frank Koehn, Fort Pierce, Fla.

[73] Assignee: Harbor Branch Oceanographic Institution, Inc., Fort Pierce, Fla.

[21] Appl. No.: 548,784

[22] Filed: Jul. 6, 1990

Related U.S. Application Data

[63] Continuation-in-part of Ser. No. 480,996, Feb. 16, 1990, Pat. No. 5,051,519.

[51] Int. Cl.$^5$ ............................................. A61K 31/35
[52] U.S. Cl. ..................................................... 514/453
[58] Field of Search ........................................ 514/453

[56] References Cited

U.S. PATENT DOCUMENTS

| 4,548,814 | 10/1985 | Rinehart, Jr. | 424/122 |
| 4,731,366 | 3/1988 | Munro et al. | 514/278 |
| 4,737,510 | 2/1988 | Rinehart, Jr. | 514/338 |
| 4,808,590 | 2/1989 | Higa et al. | 514/272 |

OTHER PUBLICATIONS

Faulkner, D. J. (1984) Natural Products Reports 1:551–598.
Faulkner, D. J. (1986) Natural Products Reports 3:1–33.
Faulkner, D. J. (1987) Natural Products Reports 4:539–576.
Uemura, D. K. Takahashi, T. Yamamoto, C. Katayama, J. Tanaka, Y. Okumura, Y. Hirata (1985) "Norhalichondrin A: An Antitumor Polyether Macrolide from a Marine Sponge," J. Am. Chem. Soc. 107:4796–4798.
Djura, P., D. B. Stierle, B. Sullivan, D. J. Faulkner, E. Arnold, J. Clardy (1980) "Some Metabolites of the Marine Sponges" *Smenospongia aurea* and *Smenospongia* (≡*Polyfibrospongia*) *echina*, J. Org. Chem. 45:1436–1441.
Luribrand, R. T., T. R. Erdman, J. J. Vollmer, P. J. Scheuer, J. Finer, J. Clardy (1979) "Ilimaquinone, a sesquiterpenoid quinone from a marine sponge," Tetrahedron 35:609–612.
Ravi, B. N., H. P. Perzanowski, R. A. Ross, T. R. Erdman, P. J. Sheuer, J. Finer, J. Clardy (1979) "Recent Research in Marine Natural Products: Puupehenones," Pure & Appl. Chem. 51:1893–1900.
Minale, L., R. Riccio, G. Sodano (1974) "Avarol, a Novel Sesquiterpenoid Hydroquinone with a Rearranged Drimane Skeleton from the Sponge *Disidea Avara*," Tetrahedron Letters 38:3401–3404.

*Primary Examiner*—Goldberg: Jerome D.
*Attorney, Agent, or Firm*—Saliwanchik & Saliwanchik

[57] ABSTRACT

Novel terpene hydroquinones have been isolated from the marine sponge *Stronglophora hartmanii*. These compounds have been found to have antiviral activity. Thus, these compounds, and derivatives thereof, can be used to treat viral infections. Additionally, the subject invention concerns the discovery that the terpene hydroquinone known as aureol has strong antiviral activity.

8 Claims, No Drawings

ANTIVIRAL TERPENE HYDROQUINONES AND METHODS OF USE

CROSS-REFERENCE TO A RELATED APPLICATION

This application is a continuation-in-part of co-pending application Ser. No. 480,996, filed Feb. 16, 1990, U.S. Pat. No. 5,051,519.

BACKGROUND OF THE INVENTION

Marine life has been the source for the discovery of compounds having varied biological activities. Some of the U.S. patents which have issued for such inventions are as follows: U.S. Pat. No. 4,548,814 for didemnins, having antiviral activity, were isolated from a marine tunicate; U.S. Pat. No. 4,731,366 discloses compounds, having antitumor properties, that were isolated from marine sponges from the genus Latrunculia; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin*. Clearly, marine sponges have proved to be a source of several bioactive compounds, and a number of publications have issued disclosing organic compounds derived from marine sponges, including Scheuer, P. J. (ed.) *Marine Natural Products, Chemical and Biological Perspectives*, Academic Press, New York, 1978-1983, Vol. I-V; Faulkner, D. J., (1984) Natural Products Reports 1: 551-598; Natural Products Reports (1986) 3: 1-33; Natural Products Reports (1987) 4: 539-576; J. Am. Chem. Soc. (1985) 107: 4796-4798. Though marine life has been the source of useful chemicals, there remains a need to discover more compounds which can be used medically to treat a wide range of diseases afflicting animals and humans.

Specifically, there is a great need for substances which can inhibit or kill viruses and retroviruses. Viruses and retroviruses are responsible for many serious diseases which cannot be effectively prevented or treated at this time. Viruses have been implicated in disorders ranging from the flu to cancer. Recently, RNA viruses have been associated with Acquired Immune Deficiency Syndrome (AIDS) and AIDS Related Complex (ARC). Specifically, the viruses responsible for these conditions are referred to as human immunodeficiency viruses (HIV). Although enormous sums of money and hours of manpower have been invested in an attempt to understand this disease, therapies and prophylactic compositions have proven to be extremely elusive.

The subject invention pertains to novel terpene-hydroquinones and the use of these compounds as antiviral and antitumor compounds. Terpene hydroquinones from the marine environment have been previously reported. See, for example, Djura et al. (1980) J. Org. Chem. 45: 1435 describing the metabolite aureol. Other examples of terpene-hydroquinones or terpene-quinones which have been reported in the literature are ilimaquinone (Luibrand et al. [1979] Tetrahedron 35: 609), puupehenone (Ravi et al. [1979] Pure Appl. Chem. 51: 1893), and avarol (Minale et al. [1974] Tetrahedron Letters 3401).

BRIEF SUMMARY OF THE INVENTION

The subject invention pertains to terpene hydroquinones having the following chemical structure:

Structure I

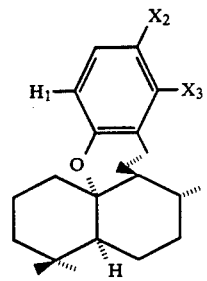

wherein $X_1$, $X_2$, or $X_3$ may be either OR or H, wherein R may be H, Ac, p-bromobenzoyl, tosyl, mesyl, or lower alkyl ($C_1$ to $C_5$).

These compounds have been found to exhibit antiviral and antitumor properties. Only one of these compounds—aureol, wherein $X_1$ and $X_3$ are H and $X_2$ is OH—has previously been described. No biological activity had ever before been attributed to aureol. An important aspect of the subject invention is the discovery that aureol exhibits strong activity against PR8 influenza and shows the ability to inhibit cell division of P388 murine tumor cells. Therefore, this compound, and derivatives thereof, can be used in the treatment of cancer and influenza infections.

The novel compounds of the subject invention have also been found to have antiviral and antitumor activity, as evidenced by their ability to inhibit replication of the PR8 virus and their ability to inhibit cell division of P388 murine tumor cells. Thus, these compounds and their analogs and derivatives can be used in the treatment of cancer and influenza infections in humans and animals.

Specifically exemplified herein are novel compounds having the structure:

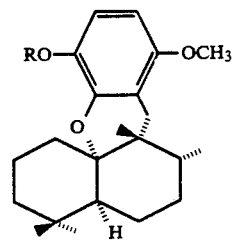

wherein R may be selected from the group consisting of H, Ac, lower alkyl, p-bromobenzoyl, tosyl, and mesyl. The following compounds are specifically exemplified:

| Compound | R |
| --- | --- |
| 1 | H |
| 2 | Ac |
| 8 | $CH_3$ |
| 9 | p-bromobenzoyl |
| 10 | tosyl, mesyl |

Further compounds of the subject invention may have the following structure:

Structure II

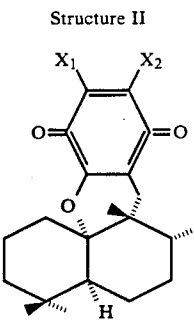

wherein $X_1$ can be H or NHR' and $X_2$ can be H, OR, or NHR' wherein R can be H, Ac, or lower alkyl and R' can be H or lower alkyl.

DETAILED DISCLOSURE OF THE INVENTION

The subject invention concerns the discovery of strong antiviral activity exhibited by the terpene hydroquinone known as aureol. This compound was originally isolated from the marine sponge *Smenospongia aureus* (Djura et al. [1980] J. Org. Chem. 45: 1435). Antiviral activity has not been previously reported for this compound.

The subject invention further pertains to novel compounds isolated from marine sponges. These compounds have also been shown to possess antiviral activity. The subject invention pertains to the compounds themselves, as well as pharmaceutical compositions containing these compounds. Also disclosed and claimed are methods for administering the novel compositions. Various derivatives of these compounds can be produced by known procedures. The compounds of interest can be isolated from marine sponges as described below.

Isolation: The sponge *Strongylophora hartmanii* was collected at a depth of 345 meters by Johnson Sea Link manned submersible at Wood Cay, Grand Bahama Island (26°44.39' N, 79°03.21' W). *S. hartmanii* is classified taxonomically as follows:
PHYLUM: Porifera
CLASS: Demospongiae
ORDER: Petrosida
FAMILY: Petrosiidae The *S. hartmanii* sample from which the novel compounds of the subject invention were isolated has the following characteristics: subspherical sponge, 3.5 cm diameter, 5 cm high, with apical oscule, 0.5 cm diameter; color is yellow-brown while alive, dark brown in ethanol; surface rugose; consistency stony; spicule type and arrangement are described by van Soest (van Soest, R. W. M. [1980] "Marine Sponges from Curacao and Other Caribean Localities. Part II: Haplosclerida," *Stud. Fauna Curacao Caribb. Isl.* 2(191): 1–173).

A specimen of this organism has been deposited in the Indian River Coastal Museum located at Harbor Branch Oceanographic Institution, 5600 Old Dixie Highway, Fort Pierce, Fl 34946. It has been assigned the identification number of IRCZM Cat. #003: 00037.

The compounds of the invention are useful for various non-therapeutic and therapeutic purposes. It is apparent from the in vitro testing that the compounds of the invention are effective for inhibiting viral replication and for controlling virus-related diseases. Specifically exemplified herein is the control of influenza viruses. Also, because of the antiviral properties of the compounds, they are useful to swab laboratory benches and equipment in a virology laboratory to eliminate the presence of viruses. As disclosed herein, they are also useful prophylactically and therapeutically for treating viral infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the viral infection, the type of host involved, its age, health, weight, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

Examples of such carriers for use in the invention include ethanol, dimethyl sulfoxide, glycerol, silica, alumina, starch, and equivalent carrier and diluents. While effective amounts may vary, as conditions in which such compositions are used vary, a minimal dosage required for antiviral activity is generally between 50 and 200 micrograms against 25–80 plaque-forming units of virus. To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compounds of the subject invention can be parenterally, orally, or topically administered to subjects requiring antiviral treatment. The active compounds may be mixed with physiologically acceptable fluids such as saline or balanced salt solutions. Also, solid formulations such as tablets or capsules can be made.

The compounds of the subject invention may be applied, for example, orally, intravenously, intramuscularly, intraperitoneally, intranasally, intradermally, or subcutaneously. The compounds of the subject invention may also be combined with other antiviral substances to provide enhanced treatment.

Following are examples which illustrate procedures, including the best mode, for practicing the invention. These examples should not be construed as limiting. All percentages are by weight and all solvent mixture proportions are by volume unless otherwise noted.

EXAMPLE 1

Isolation of Compound 1

Following is a description of the isolation of the compounds of the subject invention from *S. hartmanii*. An extract of frozen sponge (stored at −20° C. until extracted) was prepared as follows: The sponge was placed into a Waring blender with 400 ml of ethyl acetate and ground for 1-3 minutes. The sponge suspension was filtered through Whatman Number 1 filter paper. The sponge residue was then returned to the blender for further extraction. This procedure was carried out four times. The combined filtrate was then concentrated by distillation under reduced pressure to yield 2.31 g of a crude brown oil. The crude extract was chromatographed under vacuum liquid chromatographic conditions on a Kieselgel 60H stationary phase using a step gradient of ethyl acetate in heptane as eluent.

Compound 1 was eluted from the column in the fractions containing 20 and 30% ethyl acetate in heptane (v/v). These two fractions were recombined and chromatographed under vacuum liquid chromatographic conditions on a Kieselgel 60H (EM Science) stationary phase. A shallow step gradient from 100% heptane to 40% ethyl acetate in heptane was used to elute the column above. The fraction eluting with ethyl acetate-heptane (1: 9 v/v) was substantially pure (95%). This material could be further purified by HPLC on a semi-preparative (1 cm [OD] by 50 cm [1]) silica gel column (Whatman Partisil 10) using 12.5% ethyl acetate in heptane as eluent. A flow rate of 4.0 ml/minute led to a a retention time of 9 minutes (1.5 column volumes).

Other variations of this procedure for isolation would be apparent to a person skilled in this art. For example, the metabolite is very nonpolar. Thus, it could be extracted from the sponge with solvents ranging in polarity from heptane and hexanes through intermediate solvents such as the halogenated solvents, ether, or acetone, up to polar solvents such as methanol, ethanol, or isopropanol.

With regard to the chromatography, on silica gel an alternate isolation scheme could be formulated using mixtures of isooctane, heptane, ether, petroleum ether, hexanes, benzene, or toluene with the halogenated solvents (chloroform, methylene chloride, 2,2-dichloroethane) or with acetone, isopropanol, or possibly very small quantities of methanol. Less polar solvents such as methanol, acetonitrile, or tetrahydrofuran could be utilized in a reverse phase scheme. On CYANO stationary phases, mixtures of ethyl acetate, isopropanol, acetone, or the halogenated solvents and ether or heptane/hexanes/isooctane could be utilized.

EXAMPLE 2

Preparation of Derivatives

Preparation of Compound 2. Compound 2 was prepared by placing 15 mg of Compound 1 into a 1 ml reactivial containing 0.3 ml pyridine (Aldrich) and 0.3 ml acetic anhydride (Aldrich). The reaction was allowed to proceed at room temperature for 14 hours. The reaction work-up consisted of adding the reaction mixture to 5 ml of water to quench the reaction, followed by liquid-liquid extraction of the reaction product with methylene chloride. The methylene chloride phase was dried over magnesium sulfate (anhydrous), filtered, and then concentrated by distillation under reduced pressure. The reaction went essentially to completion with the acetate product partitioning cleanly into the methylene chloride.

Preparation of Compound 8. The reaction is carried out as described in Feiser, L. F., and M. Feiser (1967) *Reagents for Organic Synthesis*, Vol. 1, pp. 191-193, John Wiley and Sons, Inc., New York.

Preparation of Compounds 9 and 10. The same procedure is used as for preparation of Compound 2 except p-bromobenzoyl chloride or p-toluene sulfonyl chloride is substituted for the acetic anhydride in the procedure above. A trace of pyridine may not be necessary.

EXAMPLE 3

Spectral Data

Proton NMR data were measured on a Bruker NMR spectrometer operated at 360 MHz, carbon NMR data were measured on the same instrument operated at 90 MHz.

Compound 1: $^1$H NMR ($d_6$-benzene≈40 mg/ml [chemical shifts are concentration dependent]; 360 MHz) δ: 6.94 (d J=8.6), 6.12 (d J=8.6), 5.10 (s), 3.41 (s 3H), 3.21 (d J=7.7), 2.31 (d J=7.7), 1.86 (m 2H), 1.63 (m 3H), 1.42 (m 2H), 1.29 (m 4H), 1.08 (s 3H), 1.05 (m), 0.87 (d J=7.6 3H), 0.81 (s 3H), 0.63 (s 3H). $^{13}$C NMR ($d_6$-benzene≈400 mg/ml; 90 MHz) δ: 151.2 (s), 139.7 (s), 139.4 (s), 111.5 (d), 110.6 (s), 100.7 (d), 83.7 (s), 55.1 (q), 44.0 (d), 39.8 (d), 38.1 (s), 34.1 (t), 33.5 (s), 32.7 (t), 32.2 (q), 29.5 (t), 29.2 (q), 28.0 (t), 22.7 (t), 20.3 (q), 18.8 (t), 17.4 (q). Mass spectroscopy: (HREI, 70 eV) Molecular formula: $C_{22}H_{32}O_4$ $m/z_{calc}$=344.2353, $m/z_{obs}$=344.2357.

Compound 2: $^1$H NMR (CDCl$_3$≈20 mg/ml, 360 MHz) δ: 6.82 (d J=8.7), 6.32 (d J=8.7), 3.80 (s 3H), 3.08 (d J=16.6), 2.28 (s 3H), 2.15 (d J=16.6), 2.05 (m 2H), 1.82 (m 2H), 1.75 (m 2H), 1.60 (m), 1.49 (m 3H), 1.39 (m), 1.10 (m), 1.12 (d J=7.2 3H), 1.06 (s 3H), 0.89 (s 3H), 0.80 (s 3H). $^{13}$C NMR (CDCl$_3$≈20 mg/ml, 90 MHz) δ: 169.0 (s), 155.2 (s), 143.6 (s), 132.7 (s), 119.0 (d), 111.2 (s), 99.6 (d), 83.3 (s), 55.4 (q), 44.2 (d), 39.2 (d), 37.5 (s), 33.8 (t), 33.4 (s), 31.9 (q), 31.9 (t), 29.3 (t), 28.6 (q), 27.8 (t), 22.2 (t), 20.7 (q), 19.9 (q), 18.4 (t), 17.3 (q). Mass spectroscopy: (HREI, 70 eV) Molecular formula: $C_{24}H_{34}O_4$ $m/z_{calc}$=386.2458, $m/z_{obs}$=386.2464.

EXAMPLE 4

Antiviral Assay

The antiviral assay for influenze virus type A strain PR8 is a cytopathic effect (CPE) reduction assay based on dye uptake of normal viable cells compared to cells infected with PR8 virus. Canine kidney cells (MDCK) are infected with a viral dose that kills the cell population. Compounds with antiviral activity are identified by a decrease in CPE compared to the viral controls.

A. Cell Culture

The MDCK cell culture was obtained from the American Type Culture Collection as a frozen stock in DMSO and medium.

MDCK (Madin-Darby canine kidney cells): ATCC No. CCL 34, MDCK (NBL-2), canine kidney (*Canis familiaris*), freeze #5305, passage 53.

B. Virus

Virus was obtained from the American Type Culture Collection. Myxovirus Influenza A strain A/PR/8/34 (HINI) ATCC VR 95. Freeze-dried virus lot 15D, passage history Fe/8, M/593, Ce/172, equal quantities of allantoic fluid and 10% glucose and dextran. Original preparation contributed by A. Chappel/CDC. Isolate from patient in Puerto Rico, 1934. Francis, T., (1935) Proc. Soc. Exp. Biol. Med. 32: 1172.

C. Viral Assay

1. Preparation of expedition samples for screening
   a. Samples in ethanol, methanol, and other pretested solvents can be tested directly. Samples in solvents such as methanol/toluene mixtures must be evaporated and resuspended into an acceptable solvent.

2. Antiviral test

Tissue culture 96-well plates are planted at a cell concentration of 25,000 to 30,000 cells per well and grown for two days. Medium is withdrawn with an eight place manifold and 100 µl of maintenance medium is added to rows B, D, F, and H. In alternate rows, 100 µl of virus diluted in maintenance medium is added. After a 1 hour incubation period at 37° C., 100 µl of the test samples are added to the antiviral test well and the drug control well. It is noted that after the incubation period, the virus suspension is left on the cell layer. On day 3 the assay is read. For dilutions of the test drugs or samples, if a 10 mg per ml or 1 mg per ml suspension is submitted, the ratio of medium to drug for dilutions is 90 to 10 to obtain 100 µg or 1 µg of the test drug in the first well. From this well, 2-fold or 10-fold dilutions are prepared. Routine samples for screens are tested at 3 or 4 dilutions. Pure drugs are tested at sufficient concentrations to determine the 50% effective concentrations.

3. Results

Observe plates under the microscope for the overall condition of the MDCK cells and the progression of cytopathic effects in the viral controls. If the plates are in good condition, stain with neutral red and obtain optical density values at 540 nm wavelength.
   a. Neutral red assay: This assay is a modification of a procedure provided in detail by Dr. Ellen Borenfreund from Rockefeller University. Borenfreund, E. and J. A. Puerner (1984) J. Tissue Culture Methods 9: 7-9. Neutral (NR) prepared as a 0.4% aqueous stock solution shielded from light by foil. For assays, a 1:10 dilution is prepared in Dulbecco's PBS. Formol-calcium mixture: 1 ml 40% formaldehyde, 1 ml 10% anhydrous calcium chloride, and 98 ml water. Mixture can be prepared with 10 ml 40% formaldehyde, 10 ml 10% anhydrous calcium chloride, and 80 ml water. If the virus in the assay is a potential human hazard and not inactivated by alcohol and chlorox, these concentrations should be used. Acetic acid-ethanol mixture: 1.0 ml glacial acetic acid in 100 ml 50% ethanol.

Test

On day 3, remove fluid from plates with 8-place manifold and vacuum.
Add 0.2 ml PBS containing neutral red.
Incubate for 3 hours at 37° C.
Remove dye medium with 8-place manifold and vacuum.
Add 0.2 ml of the formol-calcium to remove unincorporated NR and enhance attachment of cells to substratum. Because fixation damages the lysosomes, limit the exposure to less than 3 minutes.
Add 0.2 ml of acetic acid-ethanol to each well and keep plate at room temperature to extract the dye. Plates are then shaken for a few seconds on the mini-shaker. Read plates on microplate reader with a 540 nm filter.

Mathematics

Controls
1 = Cells only and no NR
2 = Cells only + drug
3 = Cells only + NR
4 = Cells + NR + drug % Cytotoxicity = $[(3-1)-(4-2)/(3-2)] \times 100$ % Antiviral Activity
5 = Cells + virus + NR + drug
6 = Cells + virus + NR % Antiviral Activity = $(5/3) \times 100$
% Antiviral Activity = $(5/4) \times 100$ 0–10 = 0 Non-toxic
10–35 = 25 Marginal toxicity
36–50 = 50 Partial toxicity
51–75 = 75 Partial toxicity
76–100 = 100 Total cell kill % Antiviral To assist in visual interpretation of the data, the antiviral activity is scored from a minus to a three-plus based on the percentage of inhibition of viral cytopathic effects. Antiviral activity on crude extracts and pure samples submitted for screens is expressed using these values and the toxicity values listed above. The $EC_{50}$, representing the concentration of drug that results in a 50% reduction of the viral cytopathic effect, and the $IC_{50}$, representing the concentration of drug resulting in 50% growth inhibition, determined from graphs constructed from the raw data. The in vitro therapeutic index (TI) is the ratio of $IC_{50}/EC_{50}$.

76–100 = + + + Total inhibition of drug dose
51–75 = + + Partial inhibition
26–50 = + Partial inhibition
11–25 = +/− Partial inhibition
0–10 = − − Negative

EXAMPLE 5

Antiviral Activity

Assay data for pure compounds:
Pure Compound 1:
  PR-8:
    $EC_{50}$ = 0.15 µg per 200 µl (or 2.2 µM)
    $IC_{50}$ = 1.3 µg per 200 µl (or 19 µM)
    TI = 9
Pure Compound 2:
  PR-8:
    $EC_{50}$ = 0.01 µg per 200 µl well (or 0.15 µM)
    $IC_{50}$ = 1 µg per 200 µl (or 15 µM)
    TI = 100

EXAMPLE 6

Isolation of Aureol

A frozen sample (170 grams) of *Smenospongia aurea* (Hyatt, 1875), collected by SCUBA at a depth of 50 feet, three miles north of Sandy Point, San Salvador, Bahamas (23° 59.20' N, 74° 33.35' W) was extracted by homogenization with ethanol. Filtration of the extract followed by removal of the solvent by distillation under reduced pressure gave 3.0 grams of an oily crude extract which showed significant activity against influenza type A virus (strain PR-8). The crude material was partitioned between ethyl acetate and water to yield 699 mg and 1.3 grams of organic and aqueous soluble fractions, respectively. The organic fraction was chromatographed by vacuum liquid chromatography on silica gel (Merck Kieselgel 60H) by stepwise elution with ethyl acetate/heptane mixtures of increasing polarity. The major active fraction (164 mg) was chromatographed by HPLC on silica gel (Merck Hibar semiprep, Si 60, 7 micron) in 15% ethyl acetate-80% heptane, and monitored by UV detection at 254 nm. Final purification of the major active fraction from HPLC (111 mg) was achieved by preparative thin layer chromatography (Analtech silica gel FG, 1 mm, ethyl acetate/heptane 3:7), yielding 57.9 mg of the major PR-8 active compound. The $^1$H and $^{13}$C NMR identified the compound as aureol by comparison to literature values.

NMR Data for Aureol: LREIMS M+ m/e 314. $^1$H NMR, 360 MHz (CDCl$_3$): δ6.58 (1H, d, J=8.7 Hz), 6.55 (1H, dd, J=8.7, 2.8 Hz), 6.47 (1H, d, J=2.8 Hz), 3.35 (1H, d, J=17.1 Hz), 2.08 (2H, m), 1.94 (1H, d, J=17.1 Hz), 1.79 (1H, dt, J=13.1, 4.0 Hz), 1.78 (1H, m), 1.65 (2H, m), 1.54 (1H, qd, J=13.6, 4.5 Hz), 1.42 (2H, m), 1.33 (1H, dm), 1.17 (1H, dm), 1.08 (3H, d, J=7.5 Hz), 1.04 (3H, s), 0.92 (3H, d, J=1.0 Hz), 0.76 (3H, s); $^{13}$C NMR, 90 MHz (CDCl$_3$): δ148.3 (s), 145.7 (s), 122.1 (s), 117.2 (d), 115.1 (d), 114.0 (d), 82.3 (s), 43.9 (d), 39.2 (d), 38.0 (s), 37.3 (t), 33.9 (t), 31.8 (q), 29.8 (q), 29.2 (t), 27.8 (t), 22.2 (t), 20.2 (q), 18.3 (t), 17.3 (q).

Aureol is known to have the following structure:

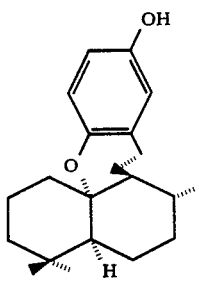

Derivatives of aureol can be readily prepared by those skilled in the art. For example, various halogen, cyano, and nitro derivatives can be prepared.

EXAMPLE 7

Antiviral Activity of Aureol

Assay data for aureol:
P388:
 IC$_{50}$=9 μg/ml
PR-8:
 EC$_{50}$=0.0063 μg per 200 μl or 0.1 μM
 IC$_{50}$=0.73 μg per 200 μl or 11.6 μM
 TI=116

We claim:

1. A process for inhibiting or killing viruses, said process comprising the administration to a person, animal or surface hosting a virus, of an effective antiviral amount of a compound having the following structure

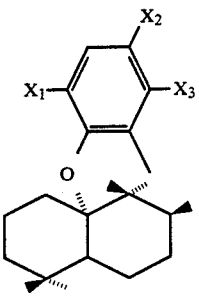

wherein X$_1$=OR or H, wherein R may be H, Ac, p-bromobenzoyl, tosyl, mesyl, or lower alkyl (C$_1$ to C$_5$); X$_2$=H or OH; and X$_3$=H or OCH$_3$.

2. The process, according to claim 1, wherein for said compound, X$_1$ is OH, X$_2$ is H, and X$_3$ is OCH$_3$.

3. The process, according to claim 1, wherein for said compound, X$_1$ is OAc, X$_2$ is H, and X$_3$ is OCH$_3$.

4. The process, according to claim 1, wherein for said compound, X$_1$ is OCH$_3$, X$_2$ is H, and X$_3$ is OCH$_3$.

5. The process, according to claim 1, wherein for said compound, X$_1$ is O-p-bromobenzoyl, X$_2$ is H, and X$_3$ is OCH$_3$.

6. The process, according to claim 1, wherein for said compound, X$_1$ is O-tosyl, X$_2$ is H, and X$_3$ is OCH$_3$.

7. The process, according to claim 1, wherein for said compound, X$_1$ is O-mesyl, X$_2$ is H, and X$_3$ is OCH$_3$.

8. The process, according to claim 1, wherein X$_1$ is H, X$_2$ is OH, and X$_3$ is H.

* * * * *

UNITED STATES PATENT AND TRADEMARK OFFICE
CERTIFICATE OF CORRECTION

PATENT NO. : 5,091,412

DATED : February 25, 1992

INVENTOR(S) : Amy E. Wright, Sue S. Cross, Neal S. Burres, Frank Koehn

It is certified that error appears in the above-identified patent and that said Letters Patent is hereby corrected as shown below:

On the title page:
[75] Inventors: "Amy S. Wright" should read --Amy E. Wright--.

Column 2: line 11 (Structure I):

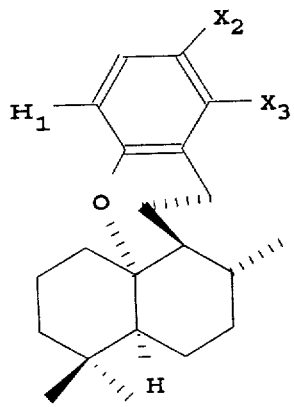 should read 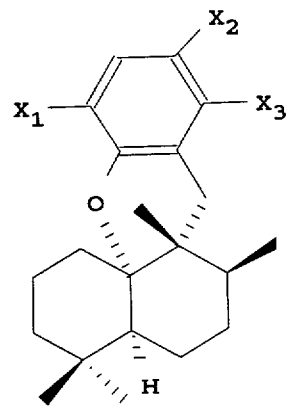

UNITED STATES PATENT AND TRADEMARK OFFICE
CERTIFICATE OF CORRECTION

PATENT NO.   :   5,091,412

DATED        :   February 25, 1992

INVENTOR(S)  :   Amy E. Wright, Sue S. Cross, Neal S. Burres, Frank Koehn

It is certified that error appears in the above-identified patent and that said Letters Patent is hereby corrected as shown below:

Column 3:   line 10 (Structure II):

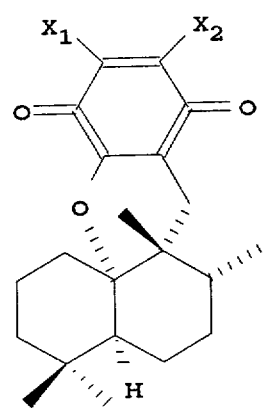   should read   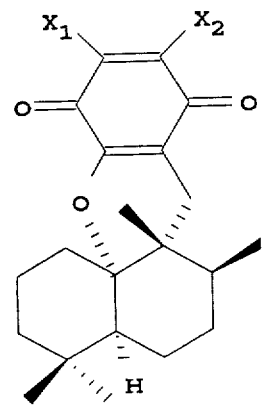

UNITED STATES PATENT AND TRADEMARK OFFICE
CERTIFICATE OF CORRECTION

PATENT NO. : 5,091,412

DATED : February 25, 1992

INVENTOR(S) : Amy E. Wright, Sue S. Cross, Neal S. Burres, Frank Koehn

It is certified that error appears in the above-identified patent and that said Letters Patent is hereby corrected as shown below:

Column 6: line 54: "influenze" should read --influenza--.
Column 8: line 40: "inhibition, determined from" should read --inhibition, are determined--.
Abstract: line 2: "*Stronglophora*" should read --*Strongylophora*--.

Signed and Sealed this

Twenty-ninth Day of June, 1993

Attest:

MICHAEL K. KIRK

*Attesting Officer*     Acting Commissioner of Patents and Trademarks